United States Patent [19]
Zheng

[11] Patent Number: 5,058,619
[45] Date of Patent: Oct. 22, 1991

[54] CONNECTOR FOR COUPLING A FLUID LINE TO A RESTERILIZABLE PORT

[75] Inventor: Zhen B. Zheng, Edison, N.J.

[73] Assignee: New Brunswick Scientific Co., Inc., Edison, N.J.

[21] Appl. No.: 591,461

[22] Filed: Oct. 1, 1990

[51] Int. Cl.$^5$ .............................................. F16K 51/00
[52] U.S. Cl. .................................. 137/240; 251/148; 137/594; 137/241
[58] Field of Search ............... 251/348, 343, 148, 345; 137/240, 241, 594, 613

[56] References Cited

U.S. PATENT DOCUMENTS

| | | | |
|---|---|---|---|
| 1,150,641 | 8/1915 | Smith | 251/148 |
| 2,298,995 | 10/1942 | Wilson | 137/241 |
| 3,517,688 | 6/1970 | Scholle | 137/240 |
| 3,643,679 | 2/1972 | Hansson | 137/241 |
| 4,169,486 | 10/1979 | Otteman et al. | 137/240 |

FOREIGN PATENT DOCUMENTS

| 829272 | 3/1960 | United Kingdom | 137/241 |
|---|---|---|---|

Primary Examiner—A. Michael Chambers
Attorney, Agent, or Firm—Mathews, Woodbridge & Collins

[57] ABSTRACT

A connector assembly for coupling a fluid transfer line to a resterilizable port. The connector assembly includes a two-position connector coupled at one end to one side of an on-off valve. At the other end, the connector has a means, e.g. threaded nut, for coupling the connector to the resterilizable port which is shown as a resterilizable spool valve. The output of the spool valve is a nipple that can be coupled to a fluid passage in the connector when the connector is placed in a first position. When so coupled, a fluid transfer passage will extend from the on-off valve through the connector and through a passage in the spool valve. The connector may be placed in a second position wherein the nipple is decoupled from the fluid passage in the connector. In this position, the assembly, i.e. spool valve and connector, can be sterilized by passing a sterilization medium, e.g. pressurized steam, through the assembly.

21 Claims, 6 Drawing Sheets

CONNECTOR FOR COUPLING A FLUID LINE TO A RESTERILIZABLE PORT

BACKGROUND OF THE INVENTION

1. Field of the Invention

The present invention relates to fluid handling equipment and, more particularly, to a connector for coupling transfer lines to a resterilizable port without the possibility of introducing contaminants into the fluid medium.

2. Description of the Prior Art

In the fields of medicine, pharmacology, biotechnology, food processing, and the like, it is often necessary to provide processing systems that are capable of handling fluids in a sterile manner. One type of processing system requiring sterile handling of fluids is a typical industrial fermentation process, a process widely used for the manufacture of drugs and food products such as alcohol, acids, cheese, etc. Because fermentation involves the controlled growth of certain living organisms, it is imperative that there be no introduction of unwanted organisms into the process. There are times, however, when it is necessary that ingredients be added to or withdrawn from the process, thereby making contamination of the process a clear possibility if proper precautions are not taken. During these periods when ingredients are added or withdrawn, special contamination problems arise primarily due to the joining and removing fluid transfer lines to process components. To prevent contamination during these periods, it is usually necessary that all lines, fittings and other fluid handling mechanisms be sterilized in some fashion while being connected.

More specifically, rubber and steel tubing have been used for years as transfer lines to transfer fluid media between containers, reactors, vessels, fermentors and other process components with the use of vessel pressurization or pumps to drive the media through the tubing. Traditionally, the tubing has been connected to component fittings with the use of a flame applied directly to the fitting just prior to connection to try and keep the connection sterile while being made. Although this technique has served the purpose, it has not proved entirely satisfactory for the reason that inconsistent sterilization results have been experienced by many users. With the flame technique, the probability of contamination often depends on the dexterity of the operator and the complexity of the fitting. Also, the use of a flame in many environments may be dangerous, while in other situations the area where the connection is to be made may be inaccessible, making the flame technique difficult to employ.

As such, those concerned with the development of fluid handling systems have long recognized the need for special inexpensive connectors capable of making a dependable sterile connection between a fluid transfer line and a process component. In addition to being inexpensive, durable and dependable, an ideal connector should be capable of being quickly coupled to the appropriate fitting with a minimum of effort on the part of the user. The present invention fulfills this need.

SUMMARY OF THE INVENTION

The general purpose of this invention is to provide a sterilizable/resterilizable quick connector for fluid transfer lines and the like. To obtain this, the present invention contemplates a unique connector assembly comprising a two-position connector and an integral on-off valve. With the connector in a first position, the assembly is connected to the appropriate process components and then sterilized while in place. After sterilization of the connector assembly, it is set in its second position to permit the process fluid to pass therethrough.

More specifically, the connector includes inner and outer telescopically mounted members. The inner member has a fluid passage extending therethrough. At one end, the inner member is joined to a fluid transfer line. Its opposite end telescopically extends into the outer member and includes a coupling orifice. The outer member has a coupling device for joining the connector to an appropriate fitting of a resterilizable port. The outer and inner members have cooperating means for setting the connector in either of the two stable positions. In the first stable position, the coupling orifice in the inner member and the port are spaced to permit resterilization of the connector. In its second stable position, the port and the orifice are coupled to permit fluid flow between the port and the fluid passage in the inner member.

It is, therefore, an object of the present invention to provide a resterilizable connector for a fluid transfer line that can be quickly connected to a resterilizable port.

Other objects and advantages of the invention will hereinafter become more fully apparent from the following description of the annexed drawings, which illustrate a preferred embodiment.

DETAILED DESCRIPTION OF THE PREFERRED EMBODIMENTS

Figure 1:
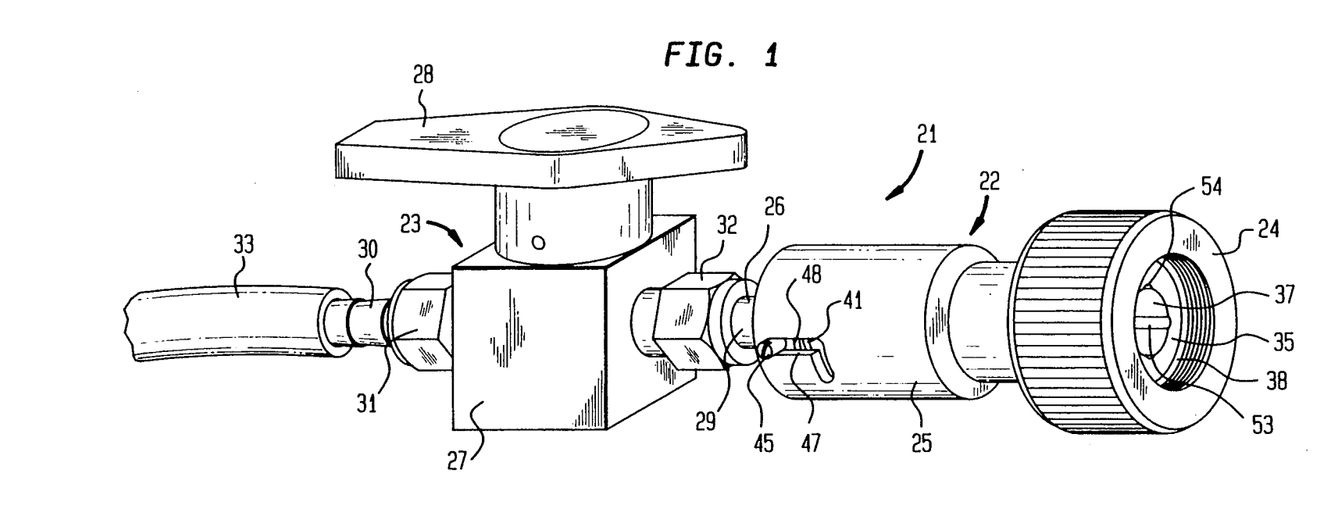
FIG. 1 shows a pictorial view of a preferred embodiment of the invention.

Referring now to the drawings, there is shown in FIG. 1 a connector assembly 21 having a two-position connector 22 and an integral on-off valve 23. The connector 22 includes a threaded nut 24 rotatably mounted on one end of a guide sleeve 25. The guide sleeve 25 is slidably and rotatably mounted on a connector body 26.

The valve 23 may be a standard manual flow control device having a valve body 27 for housing a conventional operating element (not shown), such as a needle, plug, ball, gate, etc., that is manually controlled by a handle 28. Extending from the body 27 are conventional compression fittings 31, 32. A nipple 30 has beveled ribs to form a typical friction joint for receiving the end of a flexible tube 33 such as silicon rubber tubing. Fitting 32 receives one end of a tubular projection 29 located at one end of the connector body 26.

For purposes of illustration only, it will be assumed that the valve 23 may be manually changed from fully open to fully closed or vice versa by rotating the handle 28 through a ninety degree angle. When fully open, the valve 23 will permit fluid flow in either direction between the fittings 31, 32. When fully closed no flow is permitted through the valve 23. Of course, other types of on-off valves may be employed.

Figure 2:
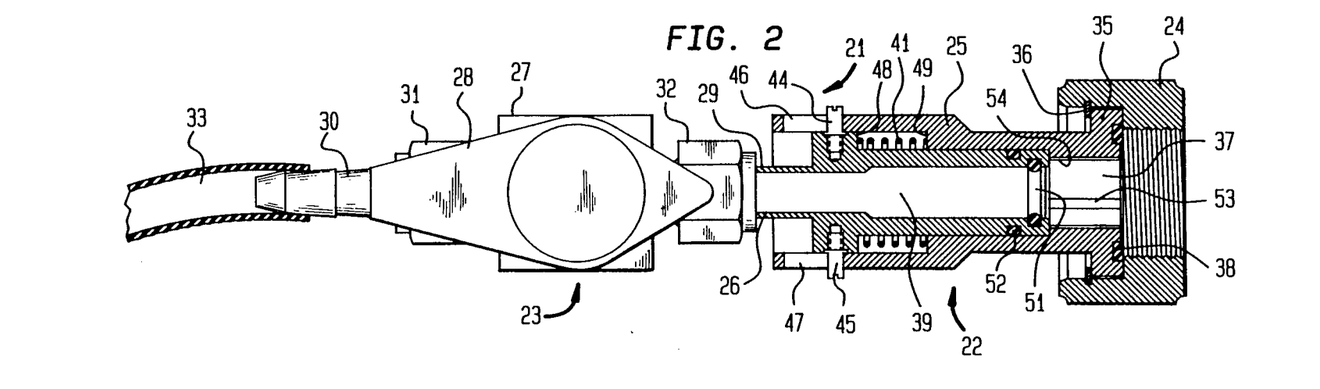
FIG. 2 illustrates a top view, partly in section, of the device shown in FIG. 1.

With particular reference to FIGS. 2-5, the structural details of connector 22 will now be described. FIG. 2 illustrates a top view of the connector assembly 21 with the connector 22 shown in cross section and the valve 23 shown in the fully open position as indicated by the position of the handle 28. The threaded nut 24 extends over an annular collar 35 formed at one end of guide sleeve 25. The nut 24 is slidably retained on the collar 35 by a retaining ring 36.

Figure 3:
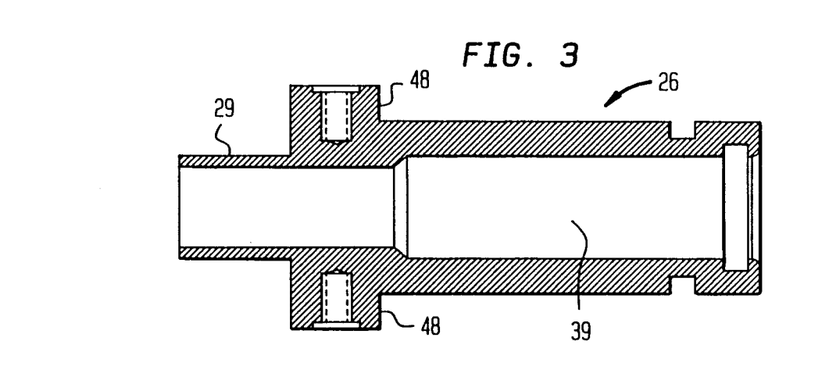
FIG. 3 is a cross-section of a portion of the device shown in FIG. 2.
Figure 4:
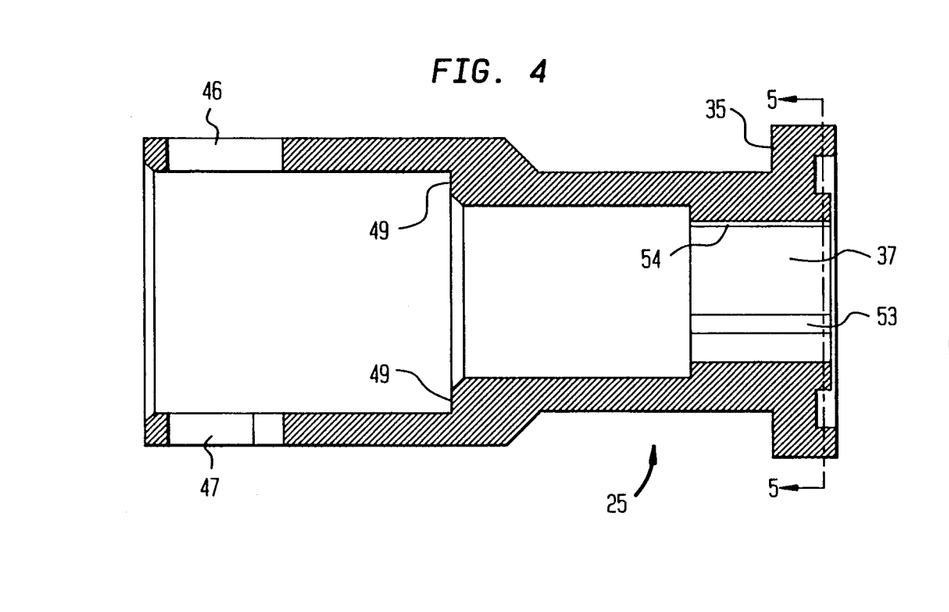
FIG. 4 is a cross-section of another portion of the device shown in FIG. 2.
Figure 5:
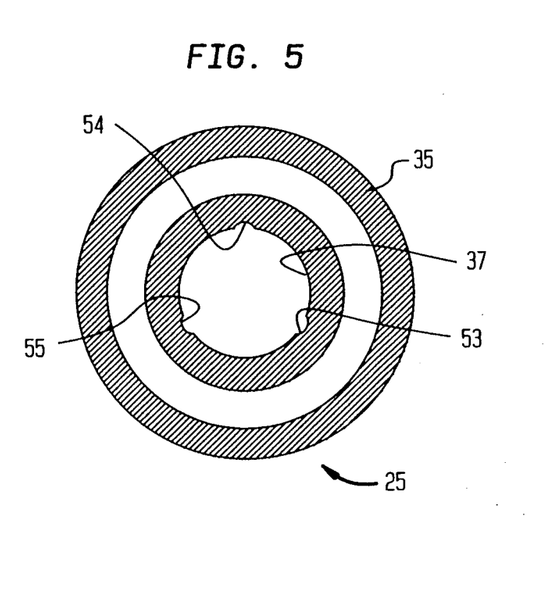
FIG. 5 is a sectional view taken on the line 5—5 of FIG. 4.

A fluid passage 37 passes through collar 35. An O-ring 38 is retained in an annular groove in the end of collar 35. The guide sleeve 25 has a hollow interior for slidably receiving connector body 26. A fluid passage 39 passes through body 26 and is aligned coaxially with the passage 37. The fluid passage 39 extends through the tubular projection 29 (FIG. 3).

A quick-release, two-position joint, formed between the body 26 and sleeve 25, includes a pair of radial posts 44, 45 fixed in bores located in the body 26. The posts 44, 45 extend into similar L-shaped slots 46, 47, respectively, formed in the wall of sleeve 25. A coil spring 41 is housed coaxially between the body 26 and sleeve 25. The coil spring 25 is compressed between opposed annular shoulders 48, 49 on the body 26 and sleeve 25, respectively, to maintain a biasing force between body 26 and sleeve 25. The body 26 has an inner O-ring 51 to effect sealing engagement with the outer surface of a fluid conduit received in passages 37 and 39 as will be described below in detail. The body 26 has an outer O-ring 52 to effect a fluid seal between the outer surface of body 26 and the inner surface of sleeve 25. As seen most clearly in FIGS. 4-5, the passage 37 has three equally spaced grooves 53, 54, 55 that run axially along the surface of passage 37 for a purpose to be described below in detail.

The quick release joint formed by slots 46, 47 and posts 44, 45 permit a user to easily set the connector 22 in one of two stable positions, the extended position and the retracted position. In the extended position (FIGS. 1 and 6), the posts 44, 45 are positioned against the end of slots 46, 47, respectively, and are held there by the force of compression spring 41 acting on shoulders 48, 49. A user may readily move the connector 22 to its retracted position by first pushing the guide sleeve 25 in a direction toward the valve 23 to further compress the spring 41 and then turning the sleeve 25 with respect to body 26 so that the posts 44, 45 enter the circumferential leg portions of the L-shaped slots 46, 47, respectively. The connector 22 is held in the retracted position by the force of spring 41 as it biases the posts 44, 45 against the surface of the circumferential leg portions of the L-shaped slots 46, 47. The user may now return the connector 22 to the extended position by simply reversing the previous operation, i.e. by twisting the sleeve 25 with respect to the connector body 26 and then permitting the posts 44, 45 to move against the end of slots 46, 47, respectively, under the force of the expanding spring 41.

Figure 6:
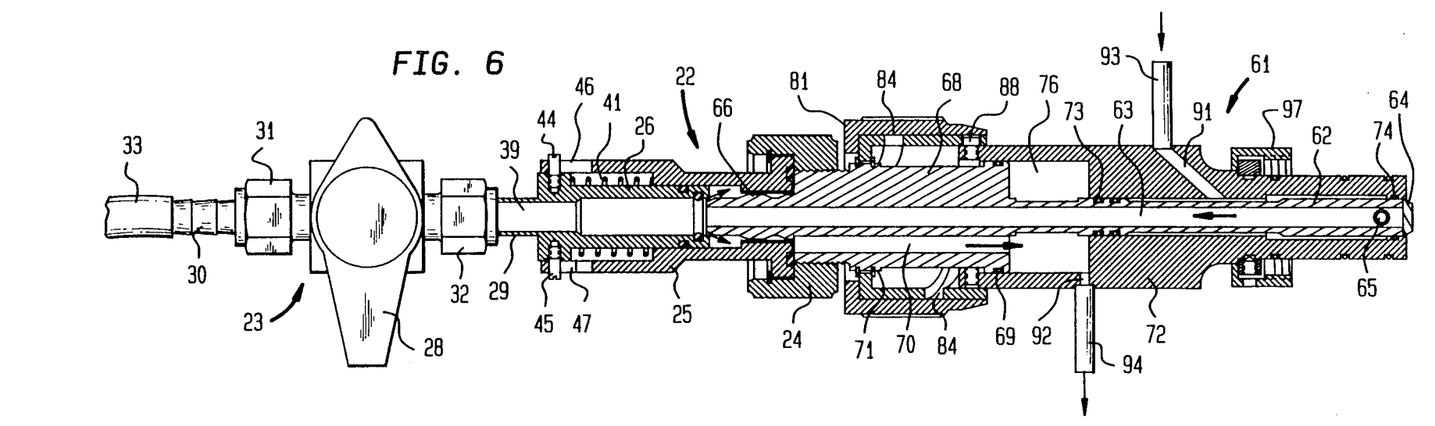
FIGS. 6 and 7 are top views, partly in section, illustrating two operating positions of the connector as it appears when connected to a resterilizable port.
Figure 7:
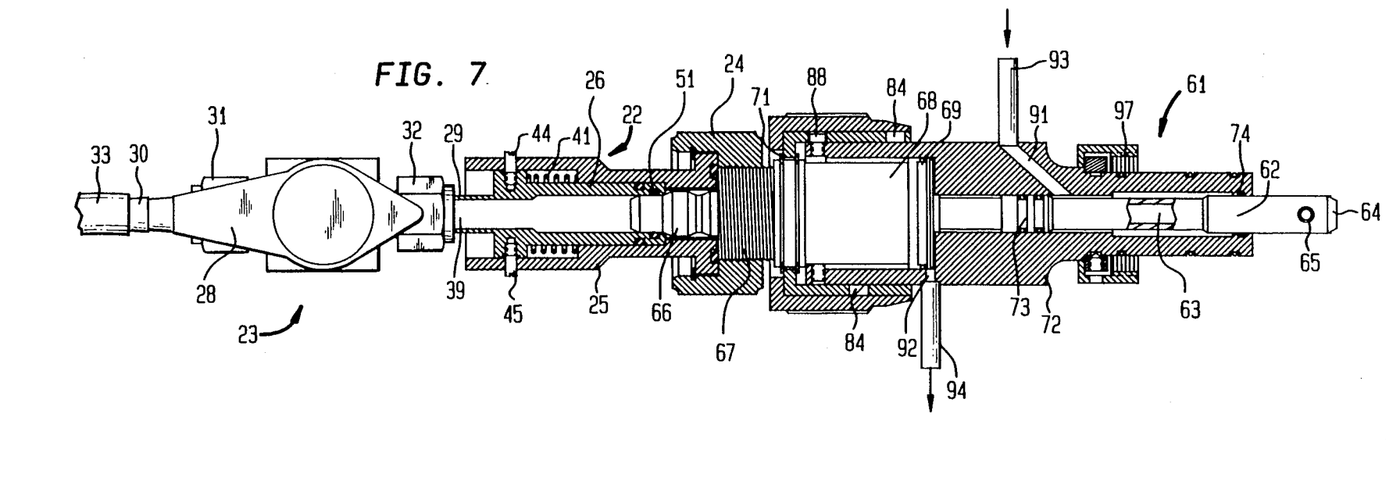

FIG. 1 depicts connector 22 in the extended position. FIG. 2 depicts the connector 22 in an unstable position wherein the posts 44, 45 are located at the intersection of the circumferential and longitudinal legs of the L-shaped slots 46, 47, respectively. FIGS. 6 and 7 illustrate the connector 22 in the extended and retracted positions, respectively.

As will be described in detail with respects to FIGS. 6 and 7, the connector 22 is designed to join one end of a transfer line, such as tube 33, to a typical resterilizable port, such as resterilizable spool valve 61, to be described below in detail. With the connector 22 set in the retracted position as shown in FIG. 7, a conduit is formed through connector 22 and valve 61 for the transfer of a fluid medium. With the connector 22 in the extended position as shown in FIG. 6, the connector 22, in cooperation with the valve 61, may be resterilized.

More specifically, FIGS. 6 and 7 illustrate a typical resterilizable spool valve 61 having a hollow spool 62 with a longitudinal passage 63 (FIG. 6) that extends substantially the length of spool 62. One end of spool 62 has an end wall 64 and adjacent transverse openings 65. The opposite end of spool 62 has a nipple 66 through which passage 63 extends. Adjacent nipple 66 the spool 62 includes an enlarged threaded portion 67.

Adjacent the threaded portion 67 is a spool head 68 having an O-ring sealing means 69 at one end and a retaining ring engaging means 71 at the other end. The spool 62 is slidably mounted in a housing 72 with O-ring sealing means 73, 74 defining a narrow chamber 75 between the inner wall of housing 72 and a portion of the outer surface of spool 62. A chamber 76 is formed between the sealing means 69, 73 and the inner surface of housing 72 and the outer surface of spool 62. A passage 70 passes through head 68 and communicates with chamber 76 at one end and at the other end communicates with a space located at one end of passage 37 (FIG. 6).

Figure 8:
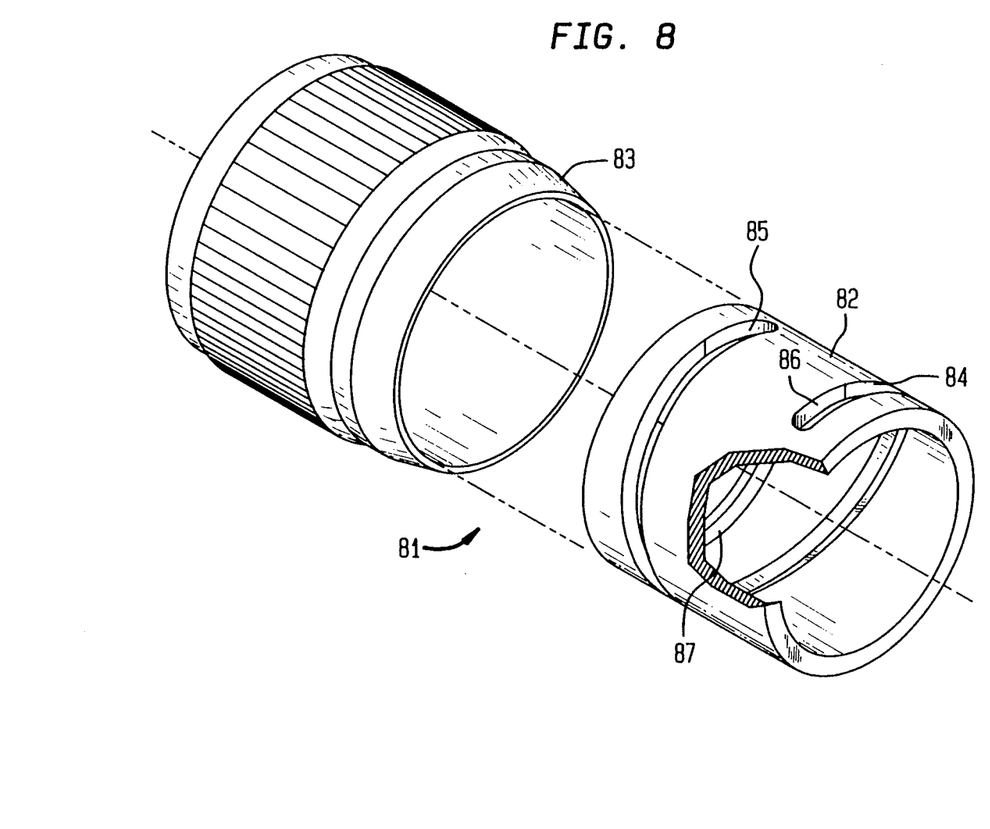
FIG. 8 is a perspective view of a portion of the device shown in FIGS. 6 and 7.

A rotatable cap 81 is composed of inner and outer sleeves 82, 83, respectively (FIG. 8). Inner sleeve 82 has a generally helical slot 84 having circumferential end portions 85, 86. The cap 81 is formed by rigidly fixing the sleeves 82, 83 together. A flange 87, on the inner sleeve 82, is rotatably fixed by a pair of retaining rings to the ring engaging means 71 of spool 62. A lug 88 is fixed to the housing 72 and has a head slidably extending into slot 84.

Inlet and outlet fluid passages 91, 92, respectively, are formed in the walls of housing 72. Inlet tube 93 is fixed to housing 72 to place tube 93 in communication with passage 91. Outlet tube 94 is fixed to housing 72 to place tube 9 in communication with passage 92. A threaded nut 97 is rotatably mounted on the outer surface of housing 72. A series of O-rings are mounted on the outer surface of housing 72 between the end thereof and the nut 97.

In operation, the end of spool valve 61 near nut 97 is inserted into a passage of a process component (not shown) for the purpose of forming a resterilizable port to the process. The nut 97 is threaded onto an appropriate fitting to secure the valve 61 to the process component. The valve 61 is opened by rotating the cap 81 to the position shown in FIG. 7, i.e. with the lug 88 resting in the circumferential end portion 85 of the slot 84. In opening valve 61, the spool 62 is moved longitudinally along the housing 72 to a position wherein the end of the spool 62 protrudes from the housing 72 and the openings 65 are located in the process (FIG. 7).

The valve 61 is closed by rotating cap 81 in the reverse direction until the lug 88 is lodged in the circumferential end portion 86 of slot 84. In the closed position the spool 62 is withdrawn into the housing 72 such that the openings 65 are withdrawn from the process.

In the open position (FIG. 7), valve 61 permits fluid to pass from nipple 66 to the process via passage 63 and openings 65. In the prior art use of valve 61, a conventional flexible tubing (e.g. tube 33) is joined to nipple 66 such that the tube would act as a transfer line connected directly to the valve 61 to add fluids to or remove fluids from the process. Fluid transfer to or from the process via valve 61 may be stopped by closing valve 61 in the manner just described, i.e. by rotating cap 81 to withdraw spool 62 into housing 72 to the closed position shown in FIG. 6.

The valve 61, when in the closed position, is designed to be resterilizable while connected to the process. However, resterilization of valve 61, in prior art applications, could only be performed before making the connection of the transfer line to the nipple 66. The manner in which such resterilization of the valve 61 takes place in prior art applications will become clear below.

In the present invention, the connector 22 is joined to the valve 61 via the nut 24 and threaded portion 67. When joined (FIGS. 6, 7), the nipple 66 extends into passage 37 and, depending on the position of connector 22, a portion of nipple 66 will or will not extend into passage 39. For example, when the connector 22 is in the extended position (FIG. 6), the nipple 66 does not extend into passage 39, but rather is spaced a small distance from body 26. However, when the connector 22 is in the retracted position (FIG. 7), the end of nipple 66 extends into passage 39 where it comes into sealing engagement with O-ring 51.

With the connector 22 coupled to the valve 61 in the manner shown in FIGS. 6, 7, the valve-connector combination may be employed to either permit the transfer of fluid between the tube 33 and the process, or to permit the resterilization of both the valve 61 and the connector 22. FIG. 7 illustrates the valve-connector combination when used to transfer fluid. In the fluid transfer position, the handle 28 is turned to place valve 23 in the open position, the connector 22 is placed in the retracted position so that nipple 66 is engaged in passage 39, and the end of spool 62 is extended from the housing 72 by setting cap 81 in the position shown (FIG. 7). As such, a fluid transfer passage exists from tubing 33 through valve 23, passage 39, passage 63 and openings 65.

FIG. 6 illustrates the valve-connector combination in the position that permits resterilization. In this position, the handle 28 is turned to close the valve 23, the connector 22 is moved to the extended position, and valve 61 is closed so that the end of spool 62 is withdrawn into the housing 72. Resterilization takes place by passing pressurized steam, or other sterilizing medium, into tube 93. The steam will flow into the passage 91 and then into the space between spool 62 and housing 72. Next the steam will flow through holes 65 into passage 63 and exit nipple 66. The steam will then flow into passage 39 up to the closed valve 23. The steam will also flow around the outer surface of nipple 66 (see arrows in FIG. 6) and into passage 37 with the help of the grooves 53, 54, 55. Finally, the steam will flow from passage 37 into passage 70 from which it will exit into chamber 76. Steam is removed from valve 61 via passage 92 and tube 94. Appropriate steam control valves (not shown) would, of course, be fixed to tubes 93, 94. Such steam control valves would be closed at all times except during resterilization. As can be seen from the above description, the steam or other sterilizing medium will sterilize the entire fluid passage from the valve 23 to the end 64 of spool 62.

When the valve 61 is used without the connector 22, as would be the case for prior art applications, and resterilization of valve 61 is desired, a cap (not shown) is threaded onto portion 67 to enclose the general area of the nipple 66. The spool 62 is withdrawn from the process to the position shown in FIG. 6 and steam is introduced into tube 93. The steam will pass through openings 65, through passage 63, into the cap (not shown), through passage 70, into chamber 76 and out tube 94. After resterilization, the steam is turned off and the cap (not shown) is removed from threaded portion 67 to permit a tubing (e.g. tube 33) to be connected to the nipple 66. However, at this point the nipple 66 and the tubing will normally be exposed to the atmosphere, thereby making contamination of the just-sterilized nipple 66 and other parts a distinct possibility. To prevent such contamination, a flame is often applied to the nipple 66 while the tubing is being connected thereto. As noted earlier, the flame process is cumbersome, is not always possible and is regarded by many to be unreliable.

In the present invention, the preferred method of perfecting a reliable sterilized connection is as follows: The tube 33, valve 23 and connector 22 are assembled with the valve 23 in the open position. This assembly is placed in an autoclave for initial sterilization. Next, the valve 23 is closed and the assembly is then removed from the autoclave and quickly coupled to the valve 61 via nut 24 and threaded portion 67. This connection is best performed quickly to reduce the degree of contamination caused by exposure to the atmosphere. The valves 23 and 61 are in the closed position (FIG. 6) at this point. The connector 22 is then placed in the extended position (FIG. 6) and steam is introduced via tube 93 to effect resterilization of both the valve 61 and connector 22. After this resterilization, the steam is shut off, the connector 22 is placed in the retracted position, valves 23 and 61 are opened, and fluid transfer may proceed without the fear of contaminating the process due to the fluid transfer components.

With the present invention a resterilization of those portions of the structure that will come into contact with the fluid medium being transferred may be reliably achieved. The connector 22 and valve 61 are capable of being quickly coupled to each other. Also, operation of the connector 22 is easy, requiring only a simply pushing and twisting motion of the guide sleeve 25 with respect to the remaining structure.

Figure 9:
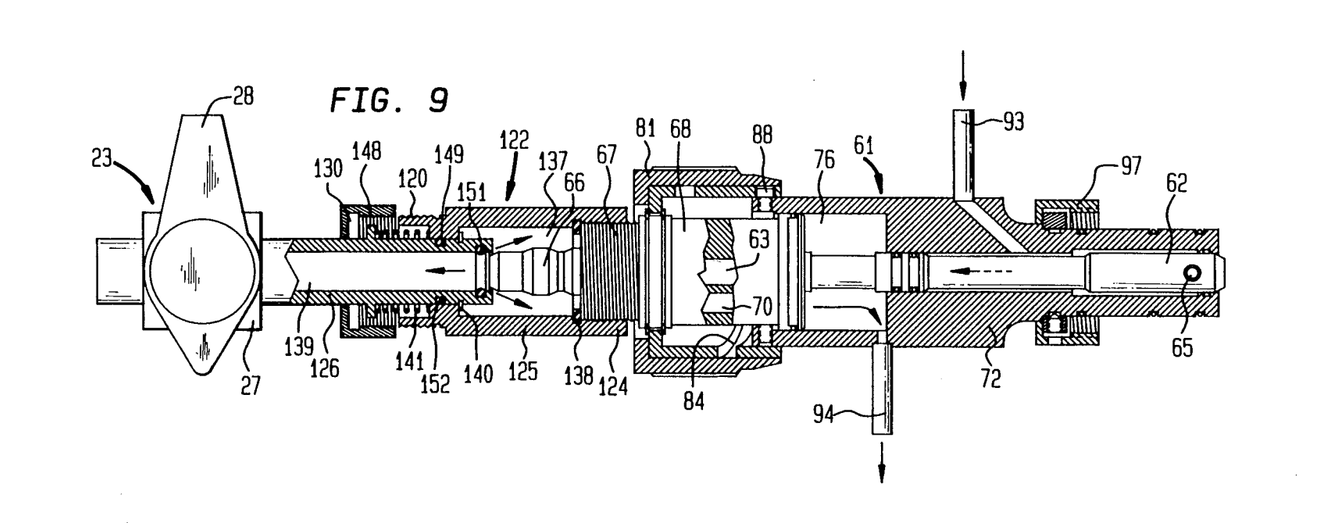
FIGS. 9 and 10 are views similar to the views shown in FIGS. 6 and 7 for a modified version of the present invention.
Figure 10:
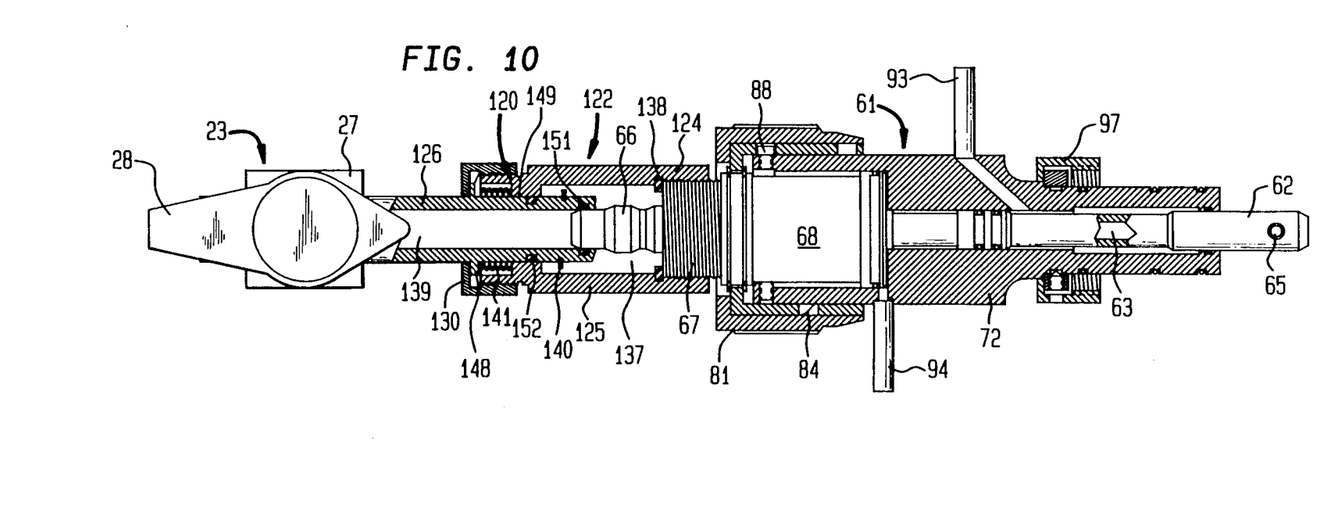

Obviously many modifications and variations of the present invention are possible in the light of the above teachings. FIGS. 9 and 10 illustrate a modified connector 122 coupled to the resterilizable spool valve 61. Connector 122 includes a guide sleeve 125 having an internal threaded portion 124 at one end for mating with the threaded portion 67 of valve 61. On O-ring 138, located in sleeve 125, forms a seal with the but end of threaded portion 67. The other end of sleeve 125 has an externally threaded portion 120 for mating with a threaded nut 130.

Nut 130 is loosely coupled about the outer surface of a connector body 126 that is telescopically mounted in sleeve 125. A coil spring 141 is mounted concentrically about the body 126 between an annular shoulder 148 on body 126 and an annular shoulder 149 on sleeve 125. A retaining ring 140, secured in a slot in the surface of body 126, cooperates with shoulder 149 to retain the body 126 in the sleeve 126. The nut 130 cooperates with shoulder 148 to force the body 126 further into the sleeve 125 as the nut 130 is threaded onto portion 120. The body 126, shown here as an integral part of the on-off valve 23, has a fluid passage 139. The sleeve 125 has a larger passage 137 in which the nipple 66 will reside.

The parts are dimensioned such that when the nut 130 is fully threaded onto portion 120, the end of nipple 66 will extend into passage 139 to form a seal with an O-ring 151 contained therein (FIG. 10). When the nut 130 is removed from portion 120 (FIG. 9), the spring 141 will force the sleeve 126 into a position wherein the nipple 66 is decoupled from passage 130. With the nipple 66 lodged in passage 130 and with the valves 23 and 61 in the open position, the connector-valve combination forms a continuous fluid passage between the valve 23 and the process. FIGS. 7 and 10 correspond to the situation wherein a fluid medium is being transferred from or to the process. Of course, transfer of the fluid medium may be terminated by simply closing valve 23 or valve 61 or both.

With both valves 23 and 61 in the closed position (FIG. 9), the assembly may be put into the resterilization position by decoupling the nut 130 from the portion 120. In the resterilization position, pressurized steam, or other sterilizing medium, is introduced into tube 93. In a manner similar to that for the FIG. 6 embodiment, the steam will flow into openings 65, through passage 63, into passage 139, through passages 137, 70, into chamber 76, and out tube 94.

Figure 11:
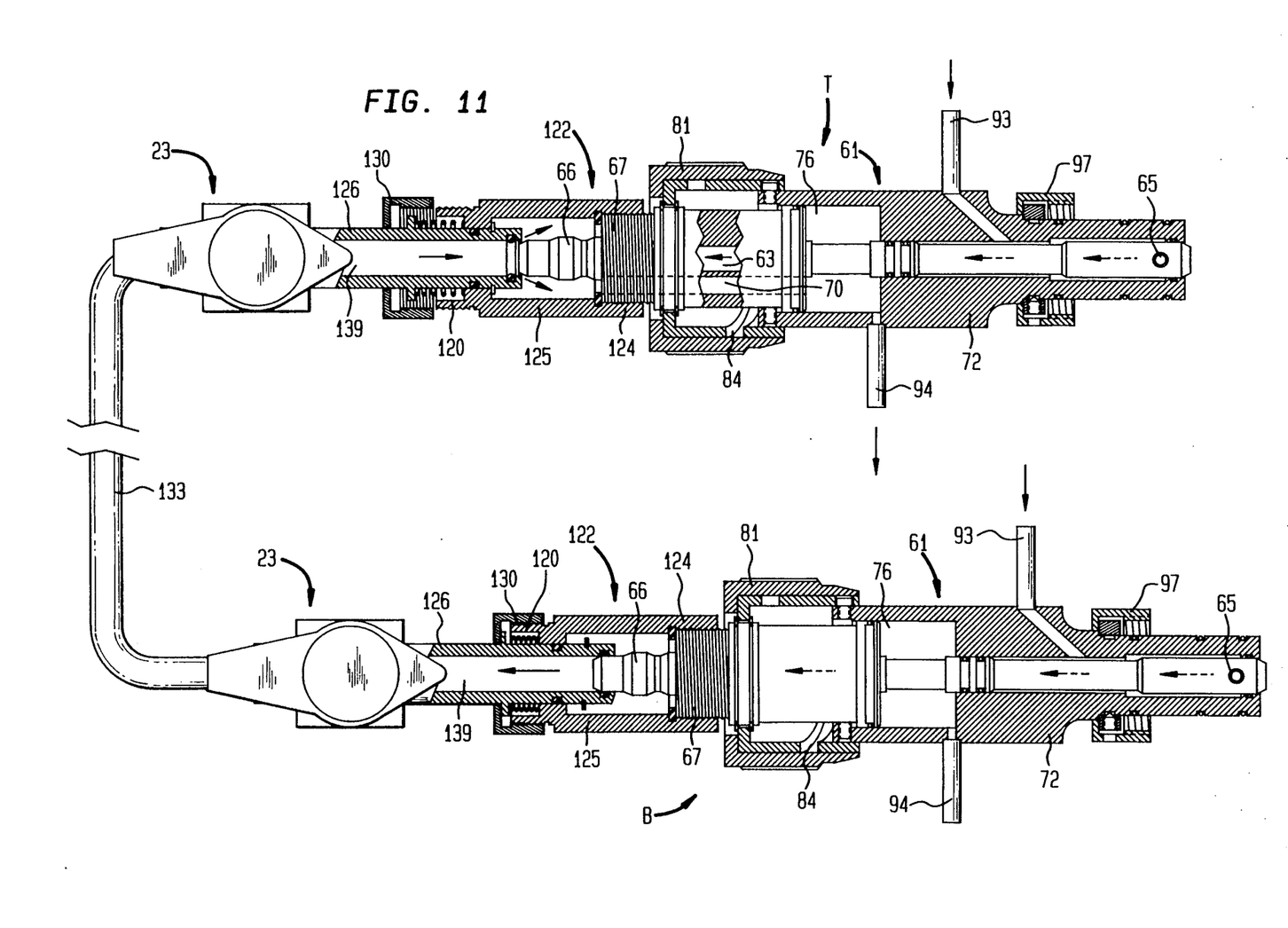
FIG. 11 is a view similar to the view in FIGS. 9 and 10 showing two connectors coupled to two resterilizable ports at opposite ends of a transfer line.

FIG. 11 illustrates a fluid transfer assembly having a transfer tube 133 and two connectors 122 coupled to either end of tube 133. Each of the valves 61 form ports on different components of the process. For example, the top assembly (T) might be connected to a fluid medium supply container while the bottom assembly (B) is connected to a fermentor.

One preferred method of forming the FIG. 11 configuration would be to first form an assembly including the tube 133 joined at either end to the valves 23 and the connectors 122. This assembly may initially be sterilized by opening both valves 23 and placing the assembly in an autoclave. After sterilization, the valves 23 are closed while the assembly is still in the autoclave. Next the assembly is removed form the autoclave and the connectors 122 are coupled to the valves 61 via the threaded portions 67, 124. At this point both valves 61 are already in the closed position. Valves 23 are now opened and one of the connectors 122 (assembly (T)) is put in the extended position, i.e. with nut 130 decoupled from portion 120. The other connector 122 (assembly (B)) is placed in the retracted position, i.e. with nut 130 coupled to portion 120. At this point, pressurized steam is introduced into tubes 93 of each of the assemblies (T), (B) while the tube 94 of assembly (T) (the one with the connector 122 extended) is opened to permit the exit of steam. The other tube 94 (assembly (B)) is closed.

With the assemblies (B), (T) and tube 133 in the position just described and as shown in FIG. 11, steam will circulate throughout the significant portions of the assemblies (T), (B), and through the tube 133. Of course, for the case where pressurized steam is used as the sterilizing medium, it will be necessary that the tube 133 and its couplings to valves 23 be sufficiently strong to withstand the significant pressures. Also, because the FIG. 11 arrangement will sterilize both connectors 122 and the tube 133 simultaneously, the original sterilization in the autoclave, as discussed above, is not necessary. Further, in the FIG. 11 configuration the valves 23 may also be eliminated if desired.

As seen from the various configurations described above, the coupling and decoupling of the fluid transfer assemblies may be performed quickly and easily. The connectors 22 and 122 are of an inexpensive, durable and dependable design. It should be understood, of course, that various other modifications are contemplated and may obviously be resorted to by those skilled in the art without departing from the spirit and scope of the invention as set forth in the appended claims.

What is claimed is:

1. A resterilizable connector-valve combination comprising:
    a resterilizable valve having a first fluid conduit means extending therethrough and a sterilization means for passing a sterilizing medium through said first fluid conduit means, wherein said first fluid conduit means has an inside surface and an outside surface;
    an outer tube;
    an inner tube having first and second orifices an a second fluid conduit means extending between said orifices, said inner tube being telescopically mounted in said outer tube with said first orifice located within said outer tube;
    coupling means on said outer tube for coupling said outer tube to said resterilizable valve with one end of the first fluid conduit means extending into said outer tube; and,
    positioning means capable of selectively holding said inner tube and said outer tube in a first stable position or in a second stable position wherein in said first stable position, said first orifice is spaced from said one end of the first fluid conduit means such that said sterilization medium sterilizes said inside and said outside surfaces of said first fluid conduit means, and wherein in said second stable position, said first orifice is coupled to said one end of the first fluid conduit means such that said sterilizing medium sterilizes said inside surface of said first fluid conduit means and does not sterilize said outside surface of said first fluid conduit means.

2. The combination of claim 1 further including an on-off valve having one side coupled to said inner tube at said second orifice.

3. The combination of claim 2 wherein said on-off valve includes means for coupling another side of said on-off valve to a fluid transfer line.

4. The combination of claim 1 wherein said positioning means includes an angled slot formed in said outer tube and a post mounted on said inner tube and extending into said slot.

5. The combination of claim 4 wherein said slot is L-shaped and has first and second angularly disposed legs.

6. The combination of claim 5 wherein said first leg extends longitudinally in the direction of said second fluid passage and said second leg extends in a lateral direction with respect to said second fluid passage.

7. The combination of claim 4 further including a spring compressed between said tubes.

8. The combination of claim 7 wherein said spring is a coil spring.

9. The combination of claim 1 wherein said positioning means includes a nut mounted on one of said tubes and a cooperating threaded portion formed on the other of said tubes.

10. The combination of claim 9 further including a spring compressed between said tubes.

11. The combination of claim 10 wherein said spring is a coil spring.

12. The combination of claim 1 wherein said coupling means includes a threaded nut.

13. A resterilizable connector-valve combination comprising:
a resterilizable valve with a first fluid passage extending between first and second ends of said resterilizable valve, and further including a first coupling means at said first end for coupling said first end to a fitting, and a second coupling means at the second end;
a fluid-line connector coupled at one end to said second coupling means, having a second fluid passage extending through said connector from said one end thereof to a second end thereof;
an on-off fluid valve coupled to said second fluid passage at said second end of said connector; and
sterilizing means for sterilizing said resterilizable valve and said fluid line connector,
wherein said connector includes positioning means for placing said connector and said valve in a first position wherein said first and second passages are spaced to permit sterilization,
and in a second position wherein said first and second passages form a continuous fluid conducting passage from said on-off valve to said first end of said resterilizable valve.

14. The combination of claim, 13 wherein said resterilizable valve is a spool valve.

15. A fluid flow system for connecting a fluid transfer line between first and second fluid locations comprising:
a fluid transfer line having first and second ends;
first and second resterilizable connectors coupled to said first and second ends, respectively;
first and second resterilizable valves connected to said first and second connectors, respectively, and having means for coupling said first and second valves to said first and second fluid locations, respectively; and
positioning means for positioning said valves and said connectors in a first stable position to permit a sterilizing medium to simultaneously pass through said valves, connectors and transfer line, while blocking said medium from entering said first and second fluid locations, and in a second stable position which permits fluid flow to occur between said first and second locations.

16. The system of claim 15 wherein said resterilizable valves are spool valves.

17. The system of claim 16 wherein said resterilizable connectors are each coupled to said first and second ends via an on-off valve.

18. A connector for connection to a fluid transportation means wherein said fluid transportation means comprises a nozzle means having an inside and an outside, said connector comprising:
an outer tube;
an inner tube, wherein said inner tube is located telescopically within said outer tube and wherein said outer tube is adapted to house said nozzle means; and
positioning means for selectively positioning said inner tube relative to said outer tube in either one of a first position and a second position, wherein said first position permits said inside and said outside of said nozzle to be sterilized and wherein said second position permits said inside of said nozzle and not said outside of said nozzle.

19. The connector of claim 18 wherein said nozzle means is sealably housed in said inner tube when said inner tube is in said second position.

20. The connector of claim 18 further comprising:
means for introducing a sterilizing medium into said connector; and wherein
in said first position said outer tube, said inner tube and said outside of said nozzle means define a space into which said sterilizing medium is capable of entering to sterilize said outside of said nozzle means.

21. A sterilizable connector for coupling to a fluid transfer line said sterilizable connector comprising:
a coupling nozzle comprising a fluid passage extending therethrough, an end portion, an inner surface and an outer surface;
an sleeve member, wherein said nozzle is mounted telescopically within said sleeve member;
a body member located with said sleeve member, said body member comprising sliding means, an inner surface and sealing means, wherein said body member is capable of sliding telescopically over the end portion of said nozzle, thus forming a seal between the outer surface of said nozzle and the inner surface of said body member; and,
locking means for selectively locking said sliding means in one of a first position or a second position, wherein said sliding means is capable of moving said body member from said first position into said second position and vice versa, and wherein in said first position there is a space between the outer surface of said nozzle means and the inner surface of said body member such that a sterilizing fluid can flow from said fluid passage into said body member and through said space over the outer surface of said nozzle means and in said second position said fluid flows directly from said fluid passage into said body member and said sealing means prevents said fluid from touching the outer surface of said nozzle means.

* * * * *